(12) United States Patent
Wallace

(10) Patent No.: US 10,161,979 B2
(45) Date of Patent: Dec. 25, 2018

(54) SYSTEM FOR PRECIPITATION-STATIC CHARGE LEVEL ESTIMATION FOR SURFACE DAMAGE TO DIELECTRICALLY COATED SURFACES

(71) Applicant: The United States of America as represented by the Secretary of the Navy, Washington, DC (US)

(72) Inventor: William W. Wallace, Gosport, IN (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 494 days.

(21) Appl. No.: 14/662,150

(22) Filed: Mar. 18, 2015

(65) Prior Publication Data

US 2015/0331028 A1 Nov. 19, 2015

Related U.S. Application Data

(60) Provisional application No. 61/954,862, filed on Mar. 18, 2014.

(51) Int. Cl.
*G01R 29/24* (2006.01)
*G01N 27/60* (2006.01)
*G01R 31/00* (2006.01)

(52) U.S. Cl.
CPC ............. *G01R 29/24* (2013.01); *G01N 27/60* (2013.01); *G01R 31/008* (2013.01)

(58) Field of Classification Search
CPC .................. G01R 29/24; G01N 27/60

USPC ........................................................ 702/58
See application file for complete search history.

(56) References Cited

U.S. PATENT DOCUMENTS

| | | | |
|---|---|---|---|
| 7,221,164 B1 | 5/2007 | Barringer | |
| 7,373,814 B1 * | 5/2008 | Brown | G01N 15/0656 73/170.17 |
| 7,592,783 B1 | 9/2009 | Jarvinen | |
| 8,410,784 B1 | 4/2013 | Brown et al. | |
| 8,723,694 B1 * | 5/2014 | Finley | B64D 45/00 340/601 |
| 2003/0071628 A1 | 4/2003 | Zank et al. | |
| 2007/0063707 A1 | 3/2007 | Van Berkel | |
| 2009/0058802 A1 * | 3/2009 | Orsley | H03K 17/975 345/157 |
| 2009/0309604 A1 | 12/2009 | Zhang | |
| 2013/0087655 A1 * | 4/2013 | Eddy | B64D 45/02 244/1 A |
| 2014/0091806 A1 | 4/2014 | Kikunaga et al. | |
| 2014/0118008 A1 | 5/2014 | Crain, Jr. et al. | |
| 2015/0331028 A1 * | 11/2015 | Wallace | G01R 29/24 702/58 |
| 2016/0031568 A1 * | 2/2016 | Yokoi | H01Q 1/281 361/218 |

OTHER PUBLICATIONS

Joseph E. Nanevicz, et al., Static-Electricity Analysis Program, Dec. 31, 1974, retrieved from http://www.dtic.mil/dtic/tr/fulltext/u2/a017873.pdf; 92 pages.

(Continued)

*Primary Examiner* — Moazzam Hossain
(74) *Attorney, Agent, or Firm* — Christopher A. Monsey

(57) ABSTRACT

A method and system for determining precipitation static charge levels on a dielectrically coated surface is provided.

9 Claims, 14 Drawing Sheets

(56) References Cited

OTHER PUBLICATIONS

Maier et al., Standardization of Precipitation Static Test Methods, Systems Engineering Test Directorate DTIC, Dec. 31, 1992, retrieved from http://www.dtic.mil/dtic/tr/fulltext/u2/a257025.pdf; 25 pages.

* cited by examiner

```
function [dataVoltage] = quick_Pstat(varargin);

if nargin==0
    distL = .38;
    startPoint = .0005;
    surfaceArea = .085;
    r1 = (startPoint+.0001):.0001:sqrt(surfaceArea/pi)-.0001;
    r2 = distL;
    resisitivityUntreated = 1.5e12;
    resisitivityTreated = 10e6;
    velocity = 434.488121; % Mach .736 at 30,000 feet, 500mph
    maxNumRandSpots = 8;
else
    return;
end
```
⎫
⎬ 103
⎭

```
chargingCurrent = [25, 50, 100, 150, 200, 250, 300 ,350, 400];

surfaceCurrent = calcIt(chargingCurrent, surfaceArea, velocity);

for k=1:1:length(r1)
    dataVoltage.surfaceIt1(:,k)= calcIt(chargingCurrent,...
    pi*((r1(k))^2), velocity);
    %surface currents induced per surface area
    % as the spot expands
    dataVoltage.surfaceIt2(:,k)= calcIt(chargingCurrent,...
    pi*(r2^(2)- (r1(k))^(2)), velocity);
    voltageUntreated = ((dataVoltage.surfaceIt1(:,k).*...
    resisitivityUntreated)./(2*pi)).*log(r1(k)/startPoint);
    currentCombined = dataVoltage.surfaceIt2(:,k)...
    +dataVoltage.surfaceIt1(:,k);
    voltageTreated = ((currentCombined.* ...
    resisitivityTreated)./(2*pi)).*log(r2/(r1(k)));
    dataVoltage.spotVoltagesBetter(:,k) = voltageUntreated+voltageTreated;
clear voltageTreated voltageUntreated currentCombined ...
    voltageTreated voltageUntreated;
end
```
⎫
⎬ 105, 107
⎭

Fig. 5A

```
for h = 1:1:randomSpotNum
    spotIt = calcIt(chargingCurrent,...
        pi*((dataVoltage.Random.Radius(h))^2), velocity);
    dataVoltage.Random.SpotCurrnets{h} = spotIt;
    dataVoltage.Random.SpotVoltages{h} = ((spotIt.*...
        resisitivityUntreated)./(2.*pi)).*log(...
        (dataVoltage.Random.Radius(h))/startPoint);
end function [Sc] = calcIt(chargingCurrent, surfaceArea, velocity)
% Calculate Current created
Sc = chargingCurrent.*surfaceArea.*(velocity./600);
    %this will result in uA units (previous line)
Sc = 1e-6.*Sc;   %change to Amps
```

```
figure(1)
plot(dataVoltage.r1(:,@),dataVoltage.spotVoltagesBetter(:,@);
hold on;
    airLineBreak = refline(0,30e3);
    set(airLineBreak,'Color','k');
    set(airLineBreak,'LineStyle',':');
    myAxis = gca;
    howLongTicksX = length(get(myAxis,'XtickLabel'));
    %set(myAxis,'XtickLabel',...
    %   0@max(dataVoltage.r1))/(howLongTicksX+1):max(dataVoltage.r1));
    myAxisXlabel = get(myAxis,'Xlabel');
    myAxisYlabel = get(myAxis,'Ylabel');
    myAxisTitle = get(myAxis,'Title');
    set(myAxis,'Yscale','log');
    set(myAxis,'NextPlot','add');
    set(myAxisXlabel,'String','Spot Radius in meters (m)');
    set(myAxisYlabel,'String','Potential in Volts (V)');
    set(myAxisTitle,'String',...
    'Spot Radius vs. Potential for charging current');
    set(myAxis,'Tag','potentials_better_vs_spot');
    legend(myAxis,strcat(num2str('chargingCurrent'),...
    ' uA/m^2'),'Location','NorthEast')
hold off;

figure(2)
lessThanOneInch = find(dataVoltage.r1<.0254);
inchLength = length(lessThanOneInch);
plot(dataVoltage.r1(:,1:1:lessThanOneInch(inchLength)),...
    dataVoltage.spotVoltagesBetter(:,1:1:lessThanOneInch(inchLength)));
hold on;
    airLineBreak = refline(0,30e3);
    set(airLineBreak,'Color','k');
    set(airLineBreak,'LineStyle',':');
    myAxis = gca;
    howLongTicksX = length(get(myAxis,'XtickLabel'));
    %set(myAxis,'XtickLabel',...
    %   0@max(dataVoltage.r1))/(howLongTicksX+1):max(dataVoltage.r1));
```

Fig. 5C

```
myAxisXlabel = get(myAxis,'XLabel');
myAxisYlabel = get(myAxis,'YLabel');
myAxisTitle = get(myAxis,'Title');
set(myAxis,'YScale','log');
set(myAxis,'NextPlot','add');
set(myAxisXlabel,'String','Spot Radius in meters (m)');
set(myAxisYlabel,'String','Potential in Volts (V)');
set(myAxisTitle,'String', ['Spot Radius vs. Potential'...
    'for charging current with spots limited to 1 Inch Radii']);
set(myAxis,'Tag','potentials_better_vs_spot');
legend(myAxis,strcat(num2str('chargingCurrent'),' uA/m^2'),...
    'Location','NorthEast')
hold off;
randomSpotNum = randi(maxNumRandSpots); %generate a random number of
    %spots with max limit of maxNumRandSpots
dataVoltage.Random.Angle = (360).*rand(randomSpotNum,1);
dataVoltage.Random.Radius = (startPoint+.0001)+ ...
    (.0127-(startPoint+.0001)).*rand(randomSpotNum,1);
dataVoltage.Random.Magnitude = (startPoint+.0001)+ ...
    ((sqrt(surfaceArea/pi)-max(dataVoltage.Random.Radius))...
    -(startPoint+.0001)).*rand(randomSpotNum,1);
```

SYSTEM FOR PRECIPITATION-STATIC CHARGE LEVEL ESTIMATION FOR SURFACE DAMAGE TO DIELECTRICALLY COATED SURFACES

CROSS-REFERENCE TO RELATED APPLICATIONS

The present application claims priority to U.S. Provisional Patent Application Ser. No. 61/954,862, filed on Mar. 18, 2014, and entitled "A SYSTEM FOR PRECIPITATION-STATIC CHARGE LEVEL ESTIMATION FOR SURFACE DAMAGE TO DIELECTRICALLY COATED SURFACES," the complete disclosure of which is expressly incorporated by reference herein.

STATEMENT REGARDING FEDERALLY SPONSORED RESEARCH OR DEVELOPMENT

The invention described herein includes contributions by one or more employees of the Department of the Navy made in performance of official duties and may be manufactured, used and licensed by or for the United States Government for any governmental purpose without payment of any royalties thereon. This invention (NC 103,102) is assigned to the United Stated Government and is available for licensing for commercial purposes. Licensing and technical inquiries may be directed to the Technology Transfer Office, Naval Surface Warfare Center Crane, email: Cran_CTO@navy.mil.

FIELD OF THE INVENTION

The present invention relates to a system for predicting theoretically achievable electrical charge levels, such as precipitation static charge, that can deposit on a dielectrically coated surface or radome, for example of an aircraft, due to precipitation static (or p-static) during flight in various conditions and at various altitudes. This in turn can be used to specify suggested coating repairs and properties thereof based upon the data generated by the system.

BACKGROUND AND SUMMARY OF THE DISCLOSURE

The surface of an aircraft, especially radomes which house antennas and other electrical equipment, may be comprised of insulating materials (e.g., dielectric materials). As an aircraft is flying, various factors, such as aircraft speed, shape of the surface, flight altitude, and weather conditions, may increase electrostatic charging on the aircraft surface. Thus, a build-up of electrical charge and, more particularly of precipitation static charge ("p-static charge"), may occur. The build-up of p-static charge may result in arcing or break overs which may interfere with the signals of the electrical equipment and/or damage the surface of the aircraft.

To prevent a build-up of p-static charge, aircraft surfaces and/or radomes may be coated with an anti-static coating. However, the anti-static coating may become worn or damaged over time, thereby leaving a portion of the aircraft surface exposed and untreated with the coating. The untreated portion of the aircraft surface is then more susceptible to a build-up of p-static charge than the coated portions of the surface. A build-up of p-static charge may result in arcing or break-overs which can create radio interference over various frequencies. Additionally, electrical discharges from the p-static charge build-up may damage the paint on the aircraft surface and/or burn holes into the surface of the aircraft. As such, aircraft surfaces may be monitored to determine if any portions of the surface are no longer coated with the anti-static coating and, therefore, may need to be repaired and/or recoated.

Historical data, measurements, or highly experienced experts have been used in the past to specify which portions of an aircraft surface and/or radome no longer include the anti-static coating. The historical measurements may determine repair size limits and materials for airborne dielectrically coated surfaces. The use of historical data may be time consuming and less accurate with respect to the actual change in composite or material properties. Measurement also is expensive and time-consuming. In addition, current measurement methodology for radomes and coated surfaces with respect to p-static performance may be inaccurate because the current measurement methodology requires measurement instruments and techniques that may alter the measurement environment and induce precision and accuracy errors. Finally, while highly experienced experts are typically quite reliable, they may not provide a scientific basis for statements on repair sizes or materials.

In one exemplary embodiment of the invention, one aspect provides plots and predicted charge levels based upon varying flight environments, flight speeds, repair sizes, or ranges of interest, as well as material properties. According to one illustrative embodiment of the present disclosure, a computer implemented system including a non-transitory computer readable storage medium storing a plurality of machine readable processing sequences is provided, wherein a user defines specific variables, and the plurality of processing sequences generates the data and plots. The estimated charge potential is shown per expanding radii of damage areas, thereby providing a prediction of the full area on the aircraft surface which may have worn or degraded anti-static coating. All areas calculated are circular so as to simplify the calculation, although the estimated charge on non-circular areas of the aircraft surface also may be determined by projected profiles with respect to the airstream in the local environment. In addition, voltage curves are plotted versus the radius of coating damage. Multiple curves are shown to represent multiple flight environments including, but not limited to, dry snow, rain, and wet snow.

The present invention may increase the efficiency and accuracy of the repair process and may increase the user base of those available to make decisions regarding damage allowances to airborne dielectrically coated surfaces.

The computer-implemented system of the present disclosure also may be used on other items where predicted breakdown on a surface is needed for determination of a static build-up. In addition, the present disclosure may be used to further compare the accepted figures and assumptions stated with the computer-implemented program to real flight data. In addition to aircrafts, the present invention may also extend to plasma based antennas which may deposit charge on the encasing or surrounding structures. Prediction of potential static build-up during rain fall and other environmental conditions may also be possible on insulated objects.

In another embodiment of the present disclosure, a computer-implemented system for determining precipitation-static charge levels on a surface includes a non-transitory computer readable storage medium having a plurality of machine readable processing sequences. The plurality of processing sequences comprise a first processing sequence that retrieves a data specification according to a plurality of commands specified by a user, a second processing sequence that generates a first matrix of values for an uncoated portion of a surface based on the data specification, a third processing sequence that generates a second matrix of values for an area of interest on the surface with an arbitrary radius of less than 0.5 inch, a fourth processing sequence that generates a first plot of values based on the first matrix, and a fifth processing sequence that generates a second plot of values based on the second matrix.

In a further embodiment of the present disclosure, a method of operating a computer-implemented system for determining precipitation-static charge on a surface comprises the steps of defining a plurality of inputs related to an aircraft surface, inputting the inputs into computer-readable instructions, comparing results generated by the computer-implemented system to material property values, determining a size and location of an uncoated portion of the surface, determining repairs for the uncoated portion, and transmitting an output including the size and location of the uncoated portion of the surface.

In another embodiment of the present disclosure, a computer-implemented system for determining precipitation-static charge levels on an aircraft surface includes an input module configured to receive information from a user regarding at least a portion of the aircraft surface, a calculation module configured to determine data values for an uncoated portion of the aircraft surface, a display module configured to transmit the data values to the user, and a determination module configured to determine repairs for the uncoated portion of the aircraft surface.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIGS. 5A-D show an embodiment of an exemplary machine readable instruction code for use with the computer-implemented system of one exemplary embodiment of the invention;

FIG. 6A shows one exemplary embodiment of a graphic user interface that may be used with one embodiment of the invention;

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Figure 1:
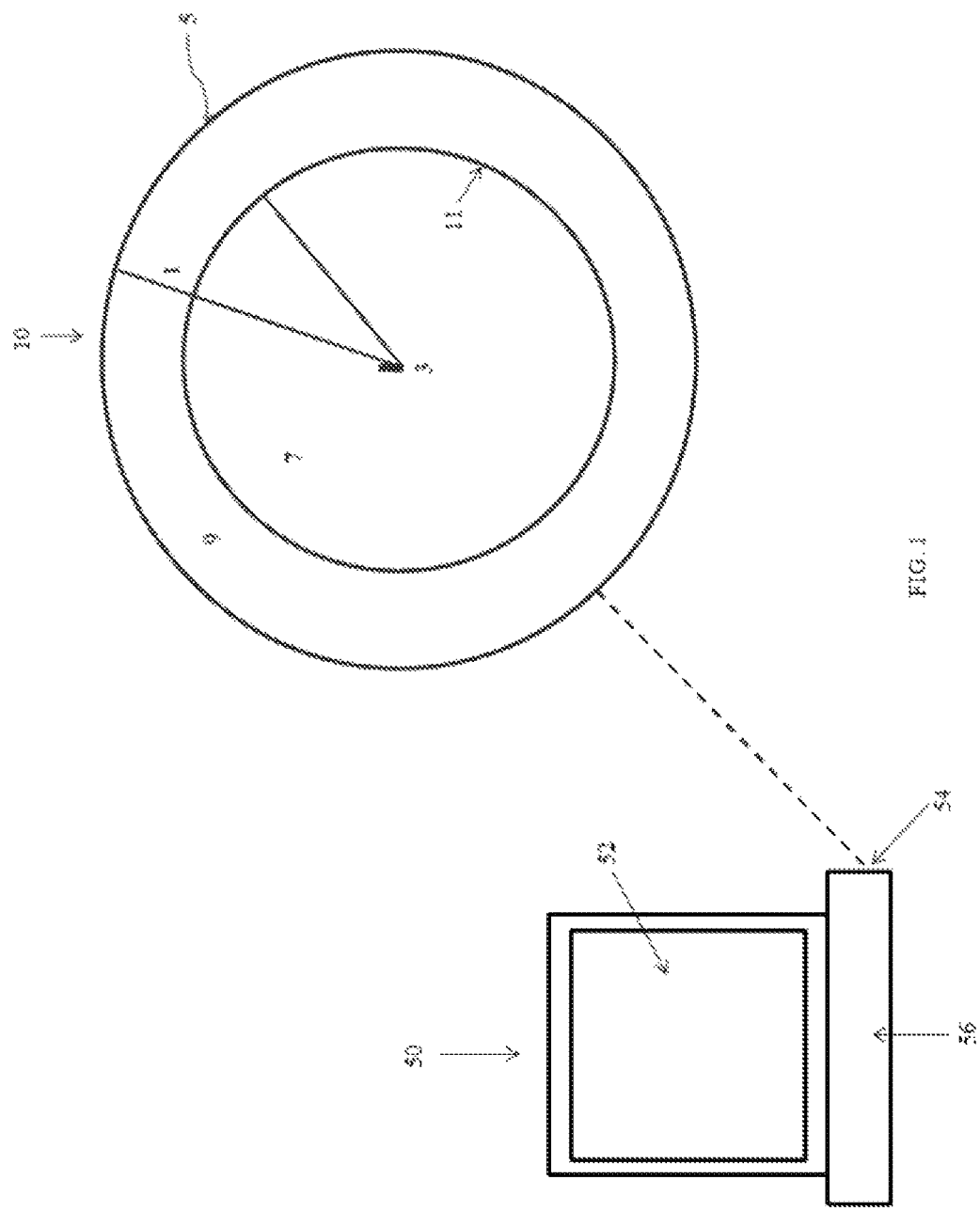
FIG. 1 shows a schematic view of a computer-implemented system which may be configured to provide a graphical description of exemplary variables on an aircraft surface in accordance with one embodiment of the invention.
Figure 2:
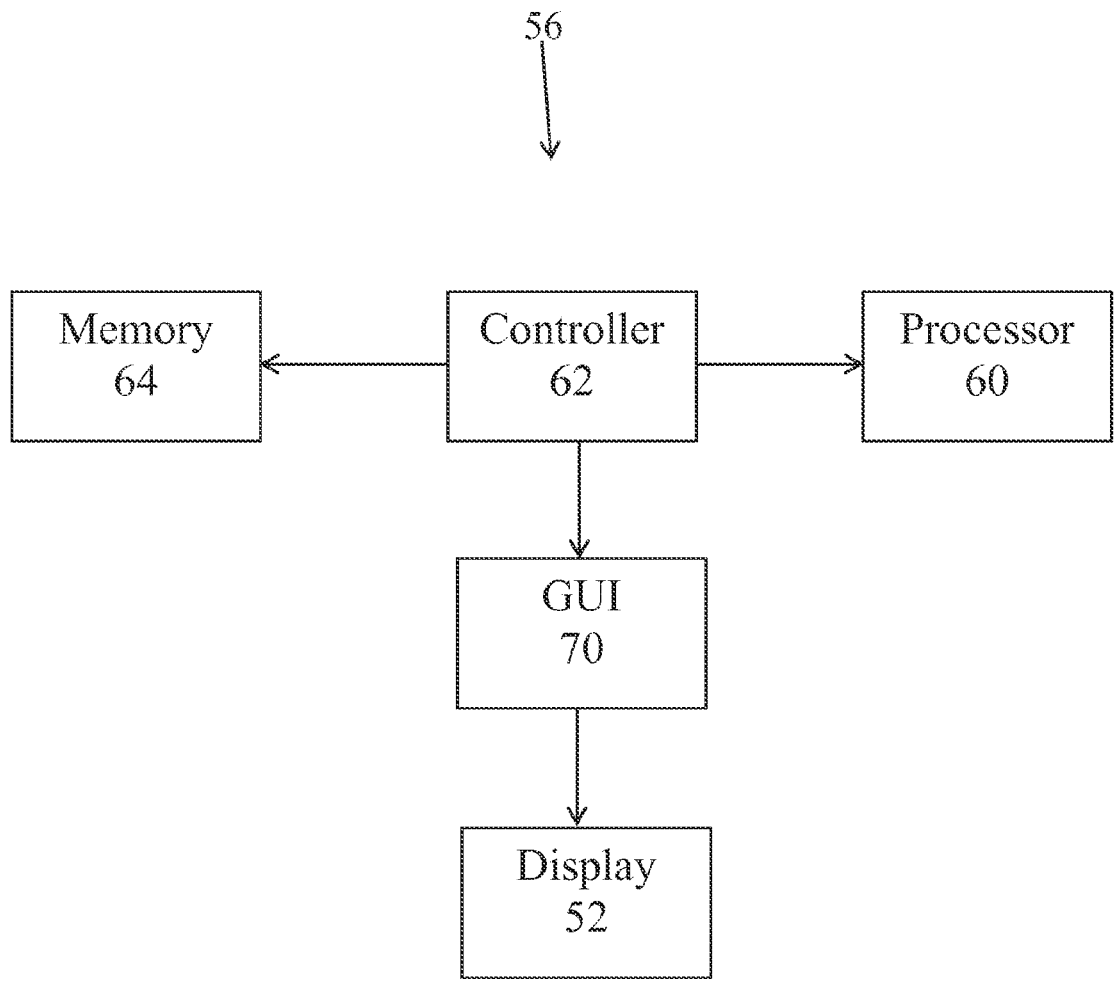
FIG. 2 shows a schematic view of the computer-implemented system of FIG. 1.

Referring initially to FIGS. 1 and 2, a computer-implemented system 50 includes a display 52, an input/output device 54 which may be wired or wireless, and a computer processing unit 56 which, as shown in FIG. 2, may include a processor 60, a controller 62, and a computer readable storage medium or memory 64 accessible by controller 62, such as a hard drive. In one embodiment, computer readable storage medium 64 is configured to store a software including a plurality of non-transitory machine-readable instructions, such as processing sequences 101 (FIGS. 4A and 4B), which may request inputs from a user through graphical user interface ("GUI") 70. Computer-implemented system 50 is configured to determine and output on display 52 a graphical representation of a surface of an aircraft 10 which is analyzed for the level of anti-static coating, damage, or other parameters. As detailed further herein, the graphical representation provides an estimated charge potential per expanding radii of a portion of aircraft surface 10 which may no longer be coated with an anti-static dielectric coating during to wear, damage, environmental conditions, and/or other factors. As such, computer-implemented system 50 is configured to determine if repairs are needed on aircraft surface 10 based on modeling predictions of how aircraft surface 10 will react at various altitudes and/or environmental conditions. In this way, computer-implemented system 50 is configured to provide a user with a computer-generated predicted probability of risk to portions of aircraft surface 10. The user then interprets the results of computer-implemented system 50 to determine what, if any, repairs are needed to aircraft surface 10 (e.g., repairs to the anti-static coating, repairs to the wall of surface 10, etc.).

Referring still to FIG. 1, computer-implemented system 50 is configured to determine a first radius 1 on aircraft surface 10 which is defined as the distance to an electrical ground point or boundary on the item or surface of interest, and is the maximum extent of the radius of the surface of interest on aircraft surface 10. Additionally, computer-implemented system 50 is configured to determine a second radius 3 which is defined as the smallest radius of a surface injection point, and is modeled as a point in space rather than an extended surface. The total surface analyzed by computer-implemented system 50 is the total surface of interest wetted or projected to the plane normal to the vector of velocity of the aircraft and is denoted as the total surface area of inspection 5. More particularly, total surface area of inspection 5 is the total area of a circle with radius 1. The surface resistivity per unit square of the aircraft surface 10 is the resistivity of an uncoated or untreated portion 7 of total surface area of inspection 5 and is shown as the smaller circle in FIG. 1. In other words, untreated portion 7 is a portion of aircraft surface 10 which does not include an anti-static dielectric coating because of damage, wear, environmental conditions, and/or other factors. Additionally, the resistivity of a treated or coated portion 9 of total surface area of inspection 5 is the surface resistivity per unit square of the coated surface within total area of inspection 5 and is shown as the larger circle in FIG. 1. In other words, treated portion 9 is a portion of aircraft surface 10 which does include an anti-static dielectric coating. As shown in FIG. 1, untreated portion 7 is generally surrounded by treated portion 9 such that only an isolated portion(s) of aircraft surface 10 may be untreated with an anti-static coating due to damage, wear, and/or environmental factors.

Figure 3:
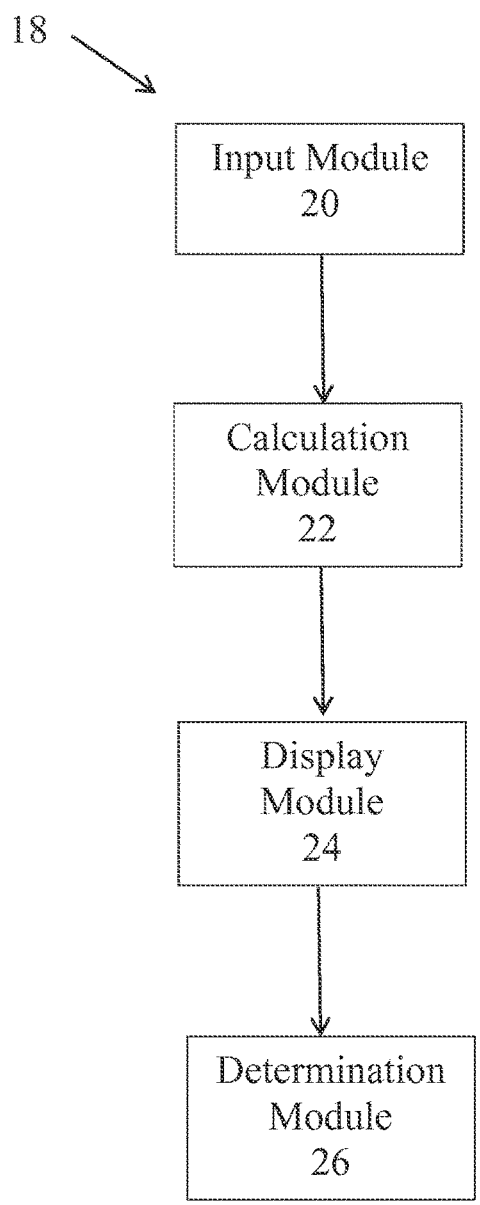
FIG. 3 shows a schematic view of a plurality of functional modules of the computer-implemented system of FIG. 1.

Referring to FIG. 3, a schematic view of a plurality of functional modules 18 is shown. The plurality of functional modules 18 define portions or segments of computer-readable instructions 101 (FIGS. 4A and 4B) and may include more than one portion of computer-readable instructions 101 and/or more than one task may be accomplished through each of the plurality of functional modules 18. Illustratively, the plurality of functional modules 18 includes an Input Module 20, a Calculation Module 22, a Display Module 24, and a Determination Module 26. Exemplary Input Module 20 and Determine Module 26 include manual steps performed by the user, whereas Calculation Module 22 and Display Module 24 include computer-implemented steps performed through computer-readable instructions 101. For Input Module 20, the user may manually input at least one variable into computer-implemented system 50, such as data points for first radius 1, second radius 3, and/or resistivity values for untreated portion 7 and treated portion 9. Additionally, in Determine Module 26, the user may manually interpret and compare the data generated by computer-implemented system 50 to determine what, if any, repairs should be made to aircraft surface 10.

FIGS. 5A-D show exemplary computer-readable instructions 101 of computer-implemented system 50. Computer-readable instructions 101 include some of the plurality of functional modules 18, specifically Calculation Module 22 and Display Module 24 (FIG. 3), and at least one code sequence or processing step is defined within each of Calculation Module 22 and Display Module 24. More particularly, after the user manually inputs variables and/or other information in sixth processing step 201 of FIG. 4B, Calculation Module 22 of computer-readable instructions 101 includes a first or input processing sequence 103 which retrieves a data specification according to a plurality of commands specified by a user, as disclosed further herein.

Calculation Module 22 includes a second or calculation processing sequence 105 of computer-readable instructions 101, in which a first matrix of values is generated for a portion of aircraft surface 10 without the anti-static dielectric coating, which reduces an accumulation of p-static charge thereon, such as untreated portion 7. The output of second processing sequence 105 is based on the data specification retrieved in first processing sequence 103. In one embodiment, second processing sequence 105 generates the first matrix of values through Equation (1), which sums together the different charge potentials of untreated portion 7 and treated portion 9 and the respective resistivity values through integration:

$$\text{Voltage} = I_t/2\pi[\rho_1 \log(r_1/r_0) + \rho_2 \log(r_2/r_1)] \quad (1)$$

where $\rho_1$ and $\rho_2$ correspond to the resistivity of untreated portion 7 and treated portion 9, respectively; $r_0$ is the entrance point of a current source, $r_1$ is an inner radius 11, defined by the outer perimeter of untreated portion 7; $r_2$ is first radius 1; and $I_t$ is calculated through Equation (2):

$$I_t = I_c \times \text{Surface Area} \times \text{Velocity}/600 \quad (2)$$

where $I_c$ is the charging parameter and 600 represents a unit conversion modifier.

Figure 4A:
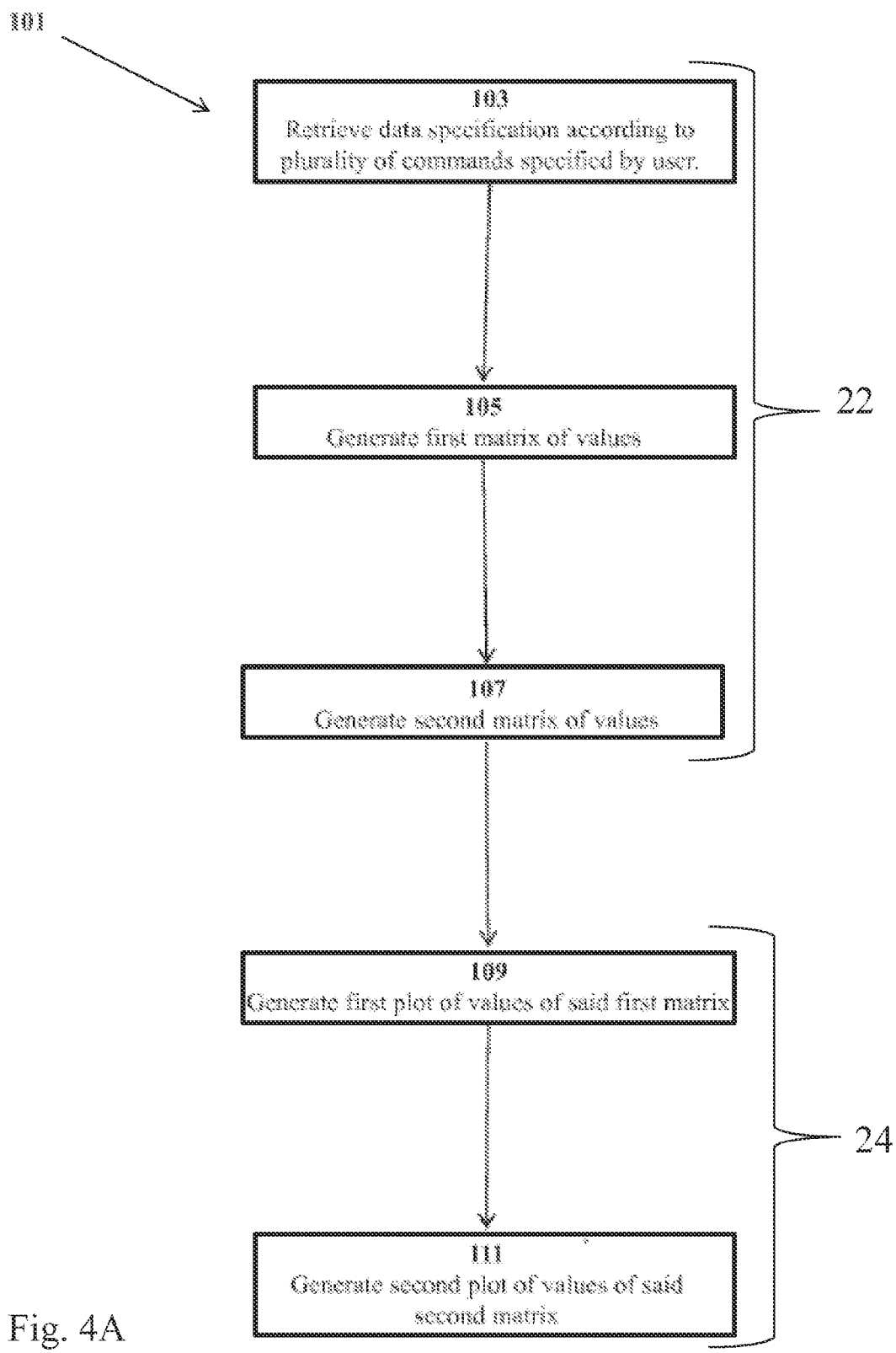
FIGS. 4A-C show an exemplary method of operation of the computer-implemented system of FIG. 1 in accordance with one exemplary embodiment of the invention.
Figure 4B:
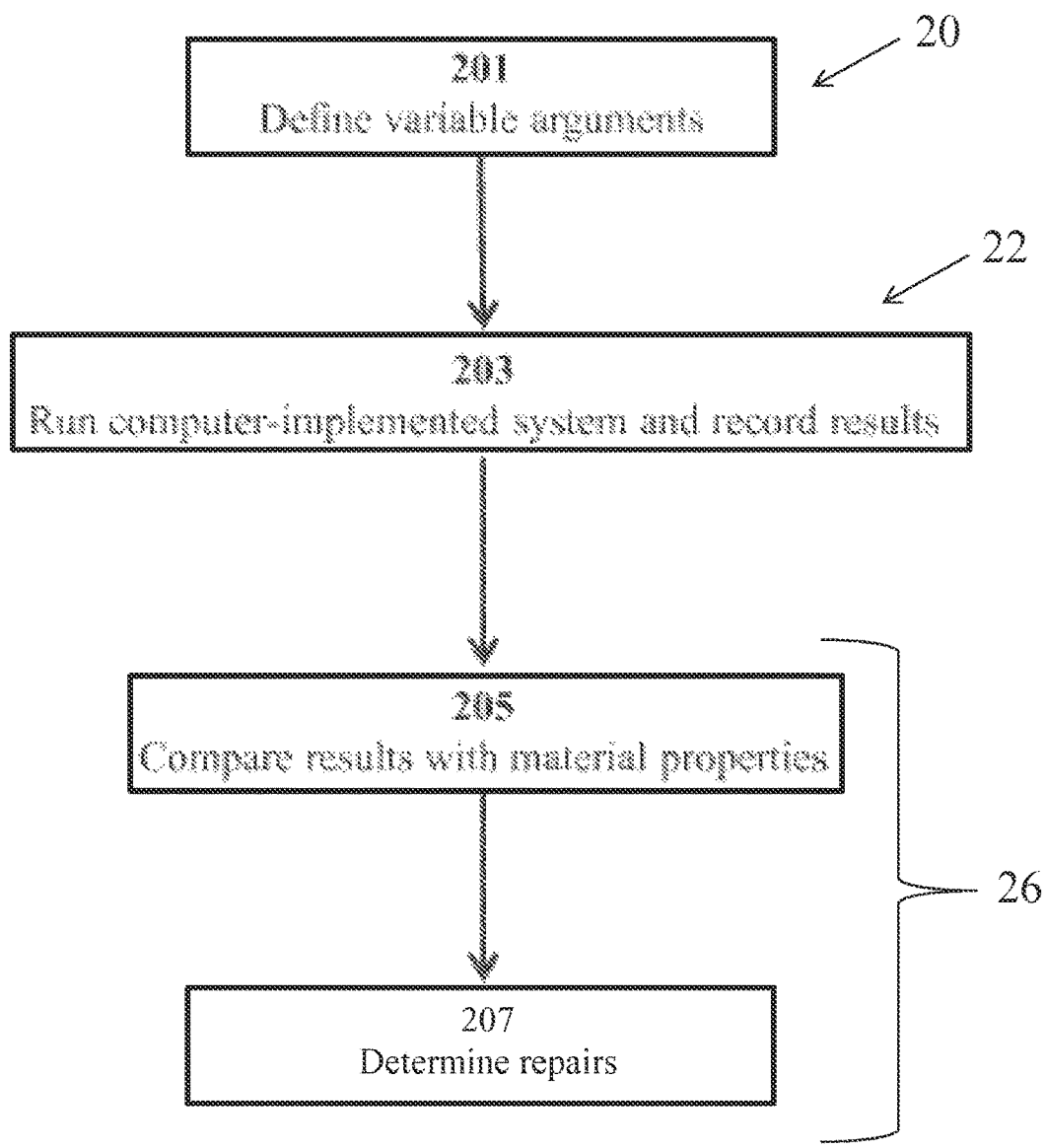

Referring still to FIGS. 4A and 4B, Calculation Module 22 of computer-readable instructions 101 also includes a third or calculation processing sequence 107 which generates a second matrix of values using Equations (1) and (2). Exemplary third processing sequence 107 limits first radius 1 of total surface area of inspection 5 to less than 0.5 inch. However, Calculation Module 22 may be modified to include inputs for first radius 1 which are greater than 0.5 inch. As such, the first matrix provides predicted levels of voltage on a portion of surface 10 defined when first radius 1 is limited to less than 0.5 inch.

Additionally, Calculation Module 22 of computer-implemented system 50 includes seventh processing step 203 (FIG. 4B) which calculates and records data and results (e.g., data and results from the first matrix and the second matrix of processing steps 105 and 107, respectively). The data and results relate to an estimated or predicted level of p-static charge on a portion of aircraft surface 10. As such, actual measurements and/or historical data are not used to determine the estimated level of p-static charge, but rather, the estimated charge potential on aircraft surface 10 is determined through theoretical calculations performed by computer-implemented system 50, which include Equations (1) and (2).

Display Module 24 of computer-readable instructions 101 includes a fourth or output processing sequence 109 which generates a plot or other output of values based on the first matrix and a fifth or output processing sequence 111 which generates a plot of values or other output values based on the second matrix. More particularly, processing sequences 109, 111 define outputs with variables such as [howLongTicksX] which specifies the lengths of the ticks on the X axis, [myAxisXlabel] which provides a label for the X axis, [myAxisYlabel] which provides a label for the Y axis, and [myAxisTitle] which provides a title for the output. Computer-implemented system 50 stores the data matrices generated by Calculation Module 22 in second processing sequence 105 and third processing sequence 107, and the data matrices can be generated by a user-generated command, which may occur through computer-implemented system 50. For example, through seventh processing step 203 of Calculation Module 22 (FIG. 4B), data and results are recorded (e.g., data and results from the first matrix and the second matrix of processing steps 105 and 107, respectively) which may be organized and presented in a visual representation of at least one plot. For example, voltage curves may be plotted versus inner radius 11 of untreated portion 7. As such, the plots which may be generated by Display Module 24 of computer-implemented system 50 compare voltage to the size of the coating damage or wear on aircraft surface 10 due to a build-up of p-static charge.

Figure 4C:
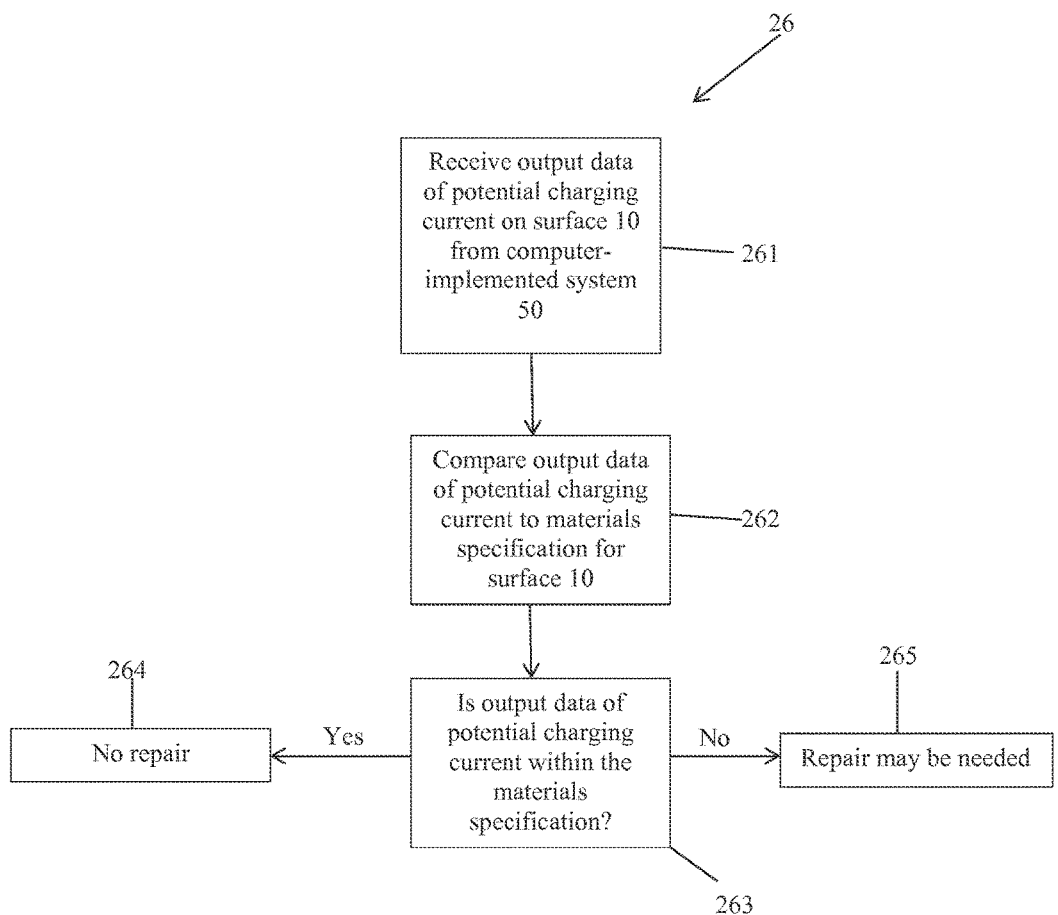

As shown in FIGS. 4B and 4C, once the results are generated in a plot or other output from computer-implemented system 50, the user compares the results with the material properties of aircraft surface 10, as shown in eighth processing step 205 of Determination Module 26. The material properties may be found in manufacturer manuals and/or materials textbooks. Referring to FIG. 4C, by comparing the results and performing other analysis, the user can determine whether any untreated portion 7 exists on aircraft surface 10 and, if so, what/if repairs should be performed based on the degradation and/or if certain altitude or weather conditions may lead to an accumulation of p-static charge on a portion of aircraft surface 10, such as untreated portion 7 (see ninth processing step 207 of Determination Module 26, shown in FIG. 4B). For example, in one embodiment, through the results and plots generated by computer-implemented system 50, the user may determine that additional anti-static coating should be applied to untreated portion 7 and, therefore, would then apply additional anti-static coating thereto according to the relevant manufacturing and repair instructions. More particularly, as shown in FIG. 4C, in Determination Module 26, a user receives output data of potential charging current on surface 10 from computer-implemented system 50 in step 261 of Determination Module 26. The user then compares the output data of potential charging current to the materials specification for surface 10, as shown in Step 262 of Determination Module 26. The user then interprets the output data of the potential charging current to determine if the data is within the materials specification for surface 10, as shown in Step 263 of Determination Module 26. Additionally, in Step 263, the user may determine if particular flight conditions (altitude, weather, etc.) may cause a build-up of p-static charge on surface 10. Lastly, if the user determines in Step 263 that the output data is within the materials specification, then no repair may be needed, as shown in Step 264. However, if the user determines in Step 263 that the output data is not within the materials specification, then repairs may be needed to surface 10, as shown in Step 265.

Build-up of p-static charge may be affected by different environments, for example altitude and weather conditions such as rain, dust, wind, snow, dry weather, and other conditions. Standards for p-static charge build-up on aircraft surface 10 may be disclosed and discussed further in MIL Standard 464A, Appendix. A plot with multiple curves may be generated by computer-implemented system 50 in order to estimate p-static charge build-up on aircraft surface 10 in various environmental conditions or based on various aircraft conditions, such as flight speed or flight altitude. For example, a plot may be generated by computer-implemented system 50 based on a flow of current per surface area (per meter squared), given the material of aircraft surface 10. In this way, computer-implemented system 50 may be utilized to estimate the point at which the breakdown voltage on aircraft surface 10 is reached.

FIGS. 5A-5D show an exemplary embodiment of computer-readable instructions 101 used to generate an output (e.g., plots) from computer-implemented system 50. Computer-implemented system 50 may be run in a variety of computer-based programs (e.g., Matlab). For example, as shown in FIGS. 5A-5D, a variety of functions are provided, such as a function [dataVoltage] which is a function for generating a plot or visual depiction of aircraft surface 10, as shown in FIG. 1, and a function for generating additional figures, plots, visual depictions, and other outputs from computer-implemented system 50. More particularly, FIGS. 5A and 5B discloses computer-readable instructions 101 for first processing sequence 103, second processing sequence 105, and third processing sequence 107. Additionally, FIG. 5C discloses computer-readable instructions 101 for fourth processing sequence 109 and a portion of fifth processing sequence 111. Additional portions of computer-readable instructions 101 for fifth processing sequence 111 are disclosed in FIG. 5D.

Figure 6A:
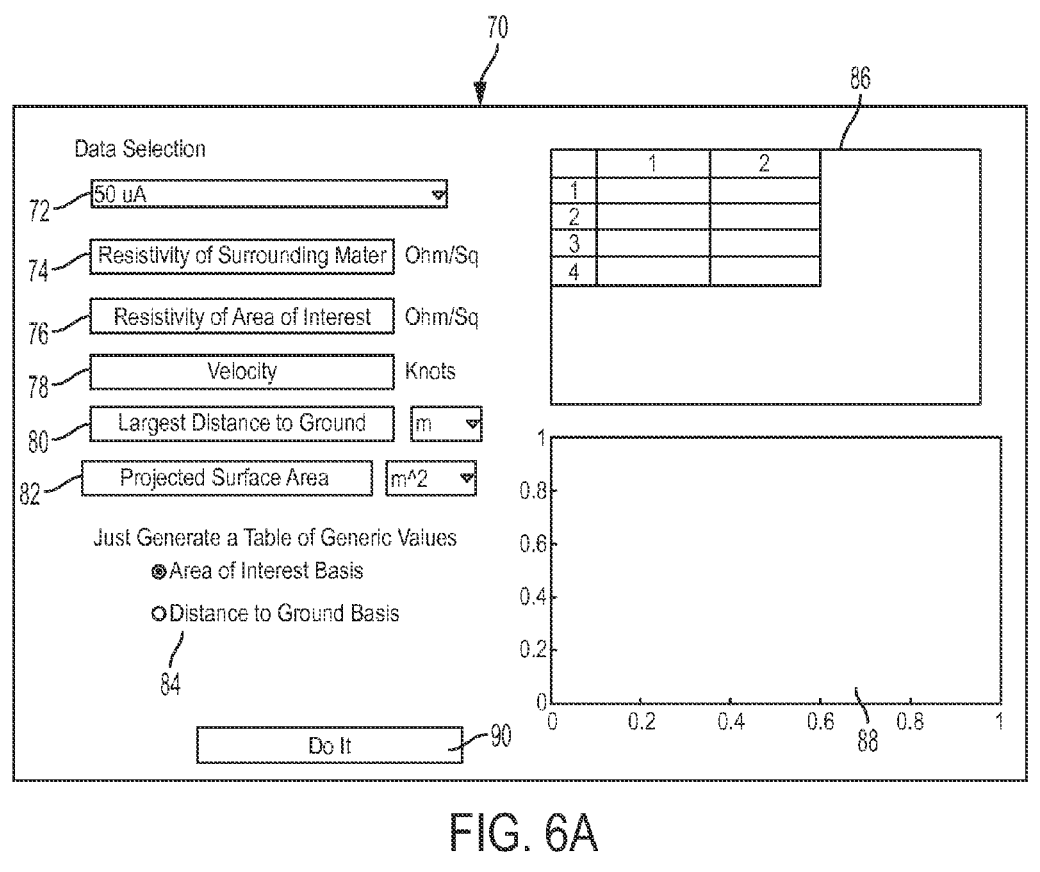
Figure 6B:
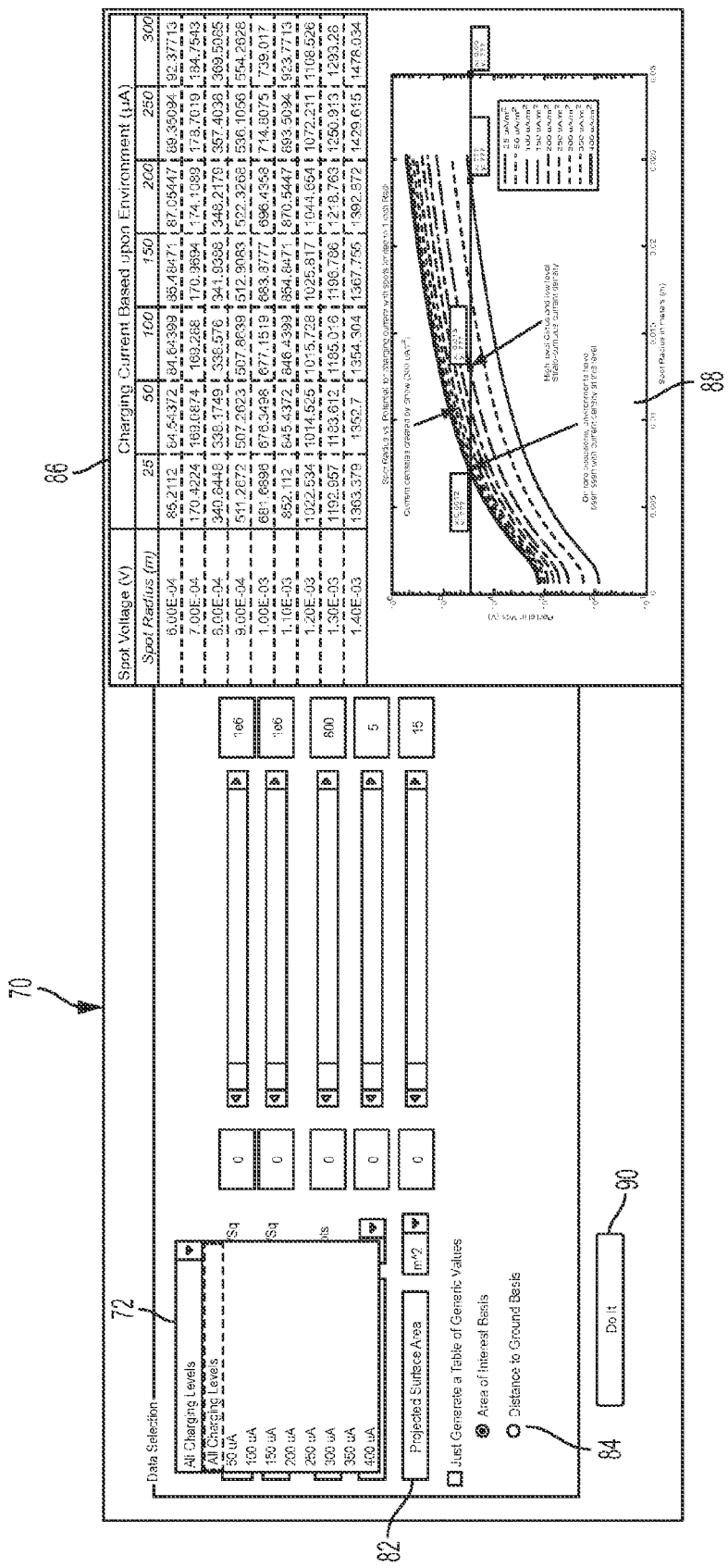
FIG. 6B shows an exemplary embodiment of the graphic user interface of FIG. 6A with at least one drop-down selection.

In order to initiate computer-implemented system 50, computer-readable instructions 101 are configured to provide a graphical user interface ("GUI") 70 on display 52 of computer-implemented system 50 for providing plots, graphical outputs, matrices, or other output displays of predicted charge level at a portion of aircraft surface 10 based on various factors, such as flight environment, velocity at aircraft surface 10, the size/radius of untreated portion 7, the size/radius of treated portion 9, and material properties. As shown in FIG. 6A, through sixth processing step 201 of Input Module 20, GUI 70 includes a selection line or portion 72 for a charging current. For example, selection line 72 for the charging current (e.g., microamps) may be a drop-down box with standard values based on different flight and/or environmental conditions from which the user selects the appropriate option, as shown in the exemplary embodiment of FIG. 6B. Additionally, GUI 70 may include a user-input line 74 for specifying a resistivity value (e.g., ohm/square unit) of treated portion 9 (FIG. 1) and a user-input line 76 for specifying a resistivity value (e.g., ohm/square unit) of untreated portion 7 (FIG. 1). GUI 70 may further include a line 78 for the user to specify a velocity (e.g., knots) at aircraft surface 10, a line 80 for the user to specify first radius 1 (i.e., the largest distance to ground, measured in meters), and a line 82 for the user to specify the projected total surface area (e.g., square meters) of inspection 5 (FIG. 1). In this way, the user may identify may identify a portion of surface 10 and, in combination with the output of computer-implemented system 50, understands where a repair may be necessary, if needed at all, and also weather and/or altitude conditions at which p-static charge may build up on surface 10. GUI 70 also includes a supplemental portion 84 for providing additional information and/or options to the user. Lines 72, 74, 76, 78, 80, and 82 and supplemental portion 84 are completed by the user during Input Module 20, and more particularly, sixth processing sequence 201, when the user manipulates GUI 70 to input various information.

The information entered by the user is then used in Calculation Module 22 when computer-implemented system 50 generates matrices of data values, as shown in second and third processing sequences 105, 107. The data values calculated by computer-implemented system 50 during Calculation Module 22 are then processed by the user in Determination Module 26. In one embodiment, the results generated through computer-readable instructions 101 are transmitted to the user and/or to a maintenance log, other personnel, or other system components for receiving, processing, and storing data regarding aircraft surface 10. In a further embodiment, computer-implemented system 50 may be configured to alert the pilot and/or a maintenance crew that the aircraft is flying through environmental conditions and/or at an altitude at which damage may occur to aircraft surface 10.

Figure 6C:
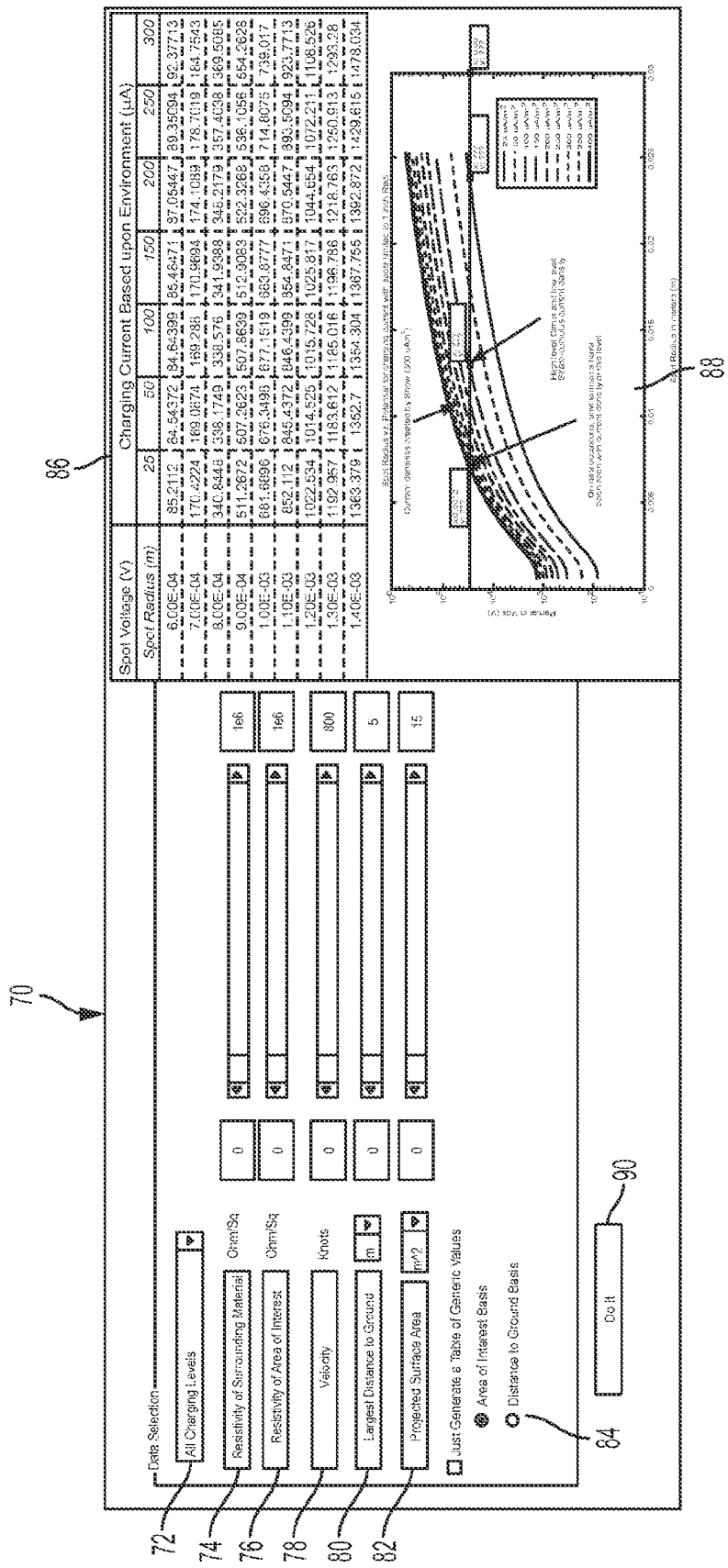
FIG. 6C shows an exemplary embodiment of the graphic user interface of FIG. 6A including a data chart in an upper output portion and a graph in a lower output portion.

GUI 70 also includes an upper output portion 86 and a lower output portion 88, both of which are configured to output a matrix, plot, visual depiction, table, graph, or other output. More particularly, upper output portion 86 is illustratively configured to display a table or chart of data which results from operation of computer-readable instructions 101 and lower output portion 88 is configured to display a further visual output of data, for example a graph or plot. For example, in the exemplary embodiment of FIG. 6C, upper output portion 86 may include a chart of spot voltage and spot radius relative to a charging current based on environmental conditions. Additionally, as shown in FIG. 6C, lower output portion 88 may include a graph of charging current vs. spot radius in various environmental conditions, according to the output in the chart of upper output portion 86. The graph in lower output portion 88 provides a user with an understanding of the vulnerable portions of aircraft surface 10 at various altitudes and/or environmental conditions. In one embodiment, the graph displayed in lower output portion 88 may include potential currents on portions of surface 10 with a radius of less than 1.0 inch. Upper and lower output portions 86, 88 display data, information, and other results in Display Module 24, and more particularly, in fourth and fifth processing sequences 109, 111. Further, GUI 70 includes an input selection or button 90, which submits the information provided in lines 72, 74, 76, 78, 80, and 82 in order to generate the outputs displayed at upper output portion 86 and lower output portion 88.

Figure 7:
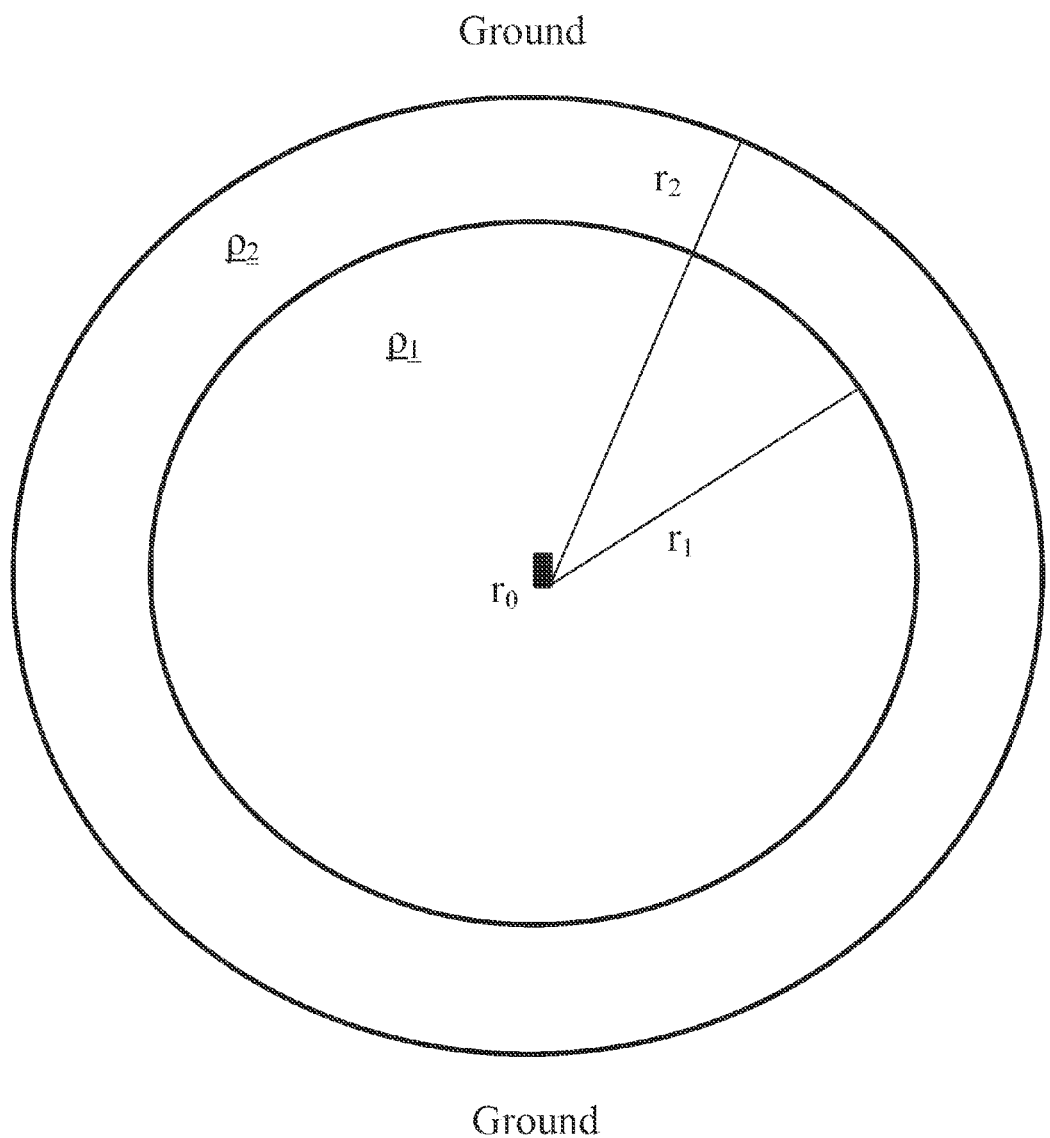
FIG. 7 shows a conceptual output adapted to facilitate display of theoretically achievable precipitation-static charge levels on a dielectrically coated surface.

In operation and as disclosed above, FIG. 7 is used as a conceptual model of aircraft surface 10 so the user is able to directly enter data variable values into computer-implemented system 50. As shown in FIGS. 5A and 5B, a user defines variables such as [distL] which is a maximum distance to an electrical ground point or boundary ($r_2$) on aircraft surface 10, as shown in FIG. 7 and disclosed in Equation (1). As shown in FIG. 5A, another variable can be [startPoint] which can be a radius less than $r_2$, such as radius $r_1$, of the surface injection point. It is to be understood that p-static charge may be deposited on a portion of or on the entire surface of aircraft surface 10 and is not merely a single injection point; however, for purposes of the calculations disclosed herein and use of computer-implemented system 50, $r_0$ discloses an injection point at which p-static charge may be present on aircraft surface 10 (e.g., untreated portion 7) due to wear or degradation in the dielectric coating present in treated portion 9. Another exemplary variable can be [surfaceArea] disclosed in FIG. 5A which can be defined as the total surface wetted or projected to the plane normal to the vector of velocity of a structure of interest. The [surfaceArea] variable can be defined as total surface area of the area of interest on aircraft surface 10. More particularly, the [surfaceArea] variable can be defined as an area of a circle with $r_2$ as its radius, as shown in FIG. 7. Another variable disclosed in FIG. 5A may be [resistivityUntreated] which can be defined as the surface resistivity per unit square of a base surface of interest (e.g., untreated portion 7) and shown as $\rho_1$ in Equation (1) and FIG. 7. Additionally, another variable disclosed in FIG. 5A may be [resistivityTreated] which may be defined as a surface resistivity per unit square of a coating surface (e.g., treated portion 9) and shown as $\rho_2$ in Equation (1) and FIG. 7. The resistivity measurements determined for treated portion 9, which includes the dielectric coating on aircraft surface 10, may be compared with the resistivity values for untreated portion 7, which is the uncoated portion of aircraft surface 10. The resistivity values $\rho_1$ and $\rho_2$ may be determined according to any known method or process for determining resistivity on a surface. Additionally, as shown in FIGS. 5A and 5B, calculation processing sequences 105, 107 of computer-readable instructions 101 generate the matrices of voltage values for untreated portion 7 and treated portion 9 of aircraft surface 10, based on variables such as [dataVoltage], [voltageTreated], and [voltageUntreated] and using the function [calcIt]. More particularly, the function [calcIt] is defined in the subroutine "function [Sc]" of FIG. 5B, which performs the calculations necessary to populate the matrices of the voltage values. Also, in one embodiment, calculation processing sequences 105, 107 include the variables [dataVoltage.Random.SpotCurrents], [dataVoltage.Random.SpotVoltages], and [dataVoltage.Random.Radius] which calculate voltages for any number of random spots within untreated portion 7 which are entered by the user.

Once the variable values required by GUI 70, disclosed in FIGS. 6A-6C, are inputted or defined by the user, computer-implemented system 50 executes computer-readable instructions 101 disclosed in FIGS. 4A-5D in order to provide at least one output to the user which defines an area of aircraft surface 10 which may have an estimated accumulation of p-static charge due to wear or degradation of the dielectric coating. With this information, the user and/or computer-implemented system 50 may be determine what/if repairs are necessary to aircraft surface 10 at untreated portion 7 to reduce or eliminate the accumulation of p-static charge. More particularly, an estimated charge potential can be determined for each unit of expanding radii on aircraft surface 10. With this information regarding the estimated charge potential at various portions of aircraft surface 10, the user determines if a portion of aircraft surface 10 has worn or degraded coating such that accumulation of p-static charge is present or likely to occur. To increase efficiency of computer-implemented system 50, areas calculated are circular, however, areas of varying shapes and sizes may be calculated with computer-implemented system 50. To provide the user with the results of the calculations of computer-implemented system 50, voltage curves may be plotted versus the radius of coating damage (i.e., radius 11 of untreated portion 7) on aircraft surface 10. Multiple curves can be shown to represent multiple flight or weather environments including, but not limited to, the estimated or actual charge on portions of aircraft surface 10 at various altitudes and in various weather environments, such as dry snow conditions, dust conditions, rain conditions, humid conditions, dry air conditions, and wet snow conditions, and any other weather condition. When computer-implemented system 50 completes the aforementioned operations, the user is provided with information about the size of a possible radome which allows the user to understand when, if, and what repairs may be done on aircraft surface 10.

Although the invention has been described in detail with reference to certain preferred embodiments, variations and modifications exist within the spirit and scope of the invention as described and defined in the following claims.

What is claimed is:

1. A computer-implemented system including a system for generating one or more graphical user interfaces on a display and determining precipitation-static charge levels on a structure comprising a substrate with a coating surrounding a surface of interest comprising a section of the substrate without the coating under specified charging environment conditions, and displaying a damage analysis output on the one or more graphical user interface based on a system that determines risks of arc over or arc through damage and graphically displaying an arc through or arc over damage risk data indicating a need for repairs to the surface based on the charge levels on the substrate surface without the coating at the specified charging environment conditions, including:

a computer readable data storage medium storing a plurality of non-transitory machine readable processing instructions configured to operate a computer processor and display outputs on a display, the plurality of non-transitory machine readable processing instructions comprising:

a plurality of initial input graphical user interface processing instructions that outputs a first plurality of graphical user interface sections on the display that receive a plurality of inputs related to a surface of interest comprising a substrate without a coating and an area surrounding the surface of interest comprising the substrate with the coating collectively having at least a greater dielectric coating than the surface of interest, the plurality of inputs comprising a first input comprising a selected charging current value selected from a drop down list of electrical charging current values created at respective predetermined altitude and environmental conditions for each electrical charging current value, a second input for a first resistivity value of the surface of interest, a third input for an atmospheric air velocity value at the surface of interest, a fourth input for a projected surface area value of the surface area of interest, a fifth input for a second resistivity value of the area surrounding the surface of interest, and a sixth input for specifying a first radius distance defined as a largest distance to an electrical ground location with respect to the surface of interest;

a plurality of input processing instructions that outputs and stores a data specification data structure on either the computer readable data storage medium or a different computer readable data storage medium according to at least the first, second, third, and fourth inputs specified by a user;

a plurality of calculation processing instructions configured to calculate a sum of a plurality of charge potentials on a portion of the surface of interest;

a plurality of output processing instructions that generates an output of values to a first output portion configured to provide a first visual output on the display, and a second output portion configured to provide a second visual output on the display, wherein at least one of a first and second output portions of a graphical user interface is determined based on the sum of the plurality of charge potentials, and the output of values includes a predicted level of precipitation-static charge on at least the portion of the surface of interest, wherein at least one of the first visual output comprises a table of spot voltage versus charging current for each of the different environmental conditions and the second visual output comprises a plurality of curves corresponding to each of the charge potentials or current density per expanding radii of the surface of interest for the different environmental conditions comprising snow, high level cirrus clouds, and low level strato-cumulus clouds; and a plurality of damage determination instructions configured to determine and display at least one correlation of arc over or arc through damage to at least the portion of the surface of interest based on the predicted level of precipitation-static charge on the surface of interest at respective specified said velocities, one or more said charging environments comprising altitude and environmental conditions for each electrical charging current value, and a size of damage to the structure defined by the surface of interest and generating a damage indicator overlay on the second visual output, wherein at least one of the first and second visual outputs includes a plurality of curves defined based on voltage versus a radius of coating damage defined by the surface of interest, wherein the plurality of curves are respectively based on multiple flight environments including dry snow, rain, and wet snow, wherein the damage indicator overlay comprises a line indicating the arc over or arc through damage occurrence at a combination of respective charging environments, velocities, and the surface of interest that is overlaid over one or more of the curves.

2. The computer-implemented system of claim 1, wherein the calculation processing instructions are configured to generate a first matrix of predicted levels of charge potentials on the surface and a second matrix of predicted levels of voltage on the surface.

3. The computer-implemented system of claim 1, wherein the plurality of damage determination instructions are further configured to display a comparison of the first and second visual outputs relative to material properties of the surface on the display.

4. The computer-implemented system of claim 1, wherein the plurality of damage determination instructions are configured to determine damage to at least a portion of the surface based on at least one of the plurality of weather conditions and the plurality of flight altitudes.

5. The computer-implemented system of claim 1, wherein a portion of the surface surrounding the uncoated portion includes a dielectric coating.

6. A method of determining and outputting data comprising occurrence of an arc over or arc through damage to a structure under specified conditions and a corresponding need to avoid exposure to such damage and repairs to the structure using a process that includes use of a computer-implemented system for determining precipitation-static charge on a surface of the structure under the specified conditions comprising the steps of:

defining a plurality of inputs related to an aircraft surface, wherein the plurality of inputs includes a first input for an electrical charge value, a second input for a resistivity value, a third input for a velocity value, and a fourth input for a surface area value;

providing a computer-implemented system for determining precipitation-static charge levels on the aircraft surface comprising a display, an input/output section, a computer processor, and a computer readable data storage medium storing a plurality of non-transitory machine readable processing instructions configured to operate at least the computer processor, the plurality of non-transitory machine readable processing instructions comprising:

a plurality of graphical user interface processing instructions that generate one or more graphical user interfaces on the display, the plurality of graphical user interface processing instructions including instructions for generating graphical user interface sections on the display that receive the first input, the second input, the third input, and the fourth input;

a plurality of input processing instructions that outputs and stores a data specification on either the computer readable data storage medium or a different computer readable data storage medium based on the first input, the second input, the third input, and the fourth input specified by a user;

a plurality of calculation processing instructions configured to calculate a sum of a plurality of charge potentials on a portion of the aircraft surface;

a plurality of output processing instructions that generates an output of values to a first output portion configured to provide a first visual output on the display, and a second output portion configured to provide a second visual output on the display, wherein at least one of a first and second output portions of the graphical user interface shown on the display is determined based on the sum of the plurality of charge potentials, and the output of values includes a predicted level of precipitation-static charge on at least the portion of the aircraft surface, wherein at least one of the first and second visual outputs further includes a plurality of curves corresponding to a voltage for a plurality of weather conditions; and a plurality of damage determination instructions configured to determine and display structural damage from arc over or arc through events to at least the portion of the aircraft surface based on the predicted level of precipitation-static charge on the surface and output another graphical user interface section showing surface damage characterization output comprising a plurality of curves defined based on voltage versus a radius of coating damage defined by the portion of the aircraft surface's dimensions, wherein the plurality of curves are respectively based on multiple flight environments including dry snow, rain, and wet snow, wherein the damage indicator overlay comprises a line indicating the arc over or arc through damage occurrence at a combination of respective charging environments, velocities, and the portion of the aircraft surface that is overlaid over one or more of the curves, wherein the plurality of damage determination instructions is further configured to compare the first and second visual outputs relative to material properties of the portion of the aircraft surface on the display;

inputting the first input, the second input, the third input, and the fourth input into the computer implemented system;

generating and displaying results of predicted voltage levels on at least the portion of the aircraft surface in at least one of said graphical user interface sections;

generating and displaying a predicted level of precipitation-static charge on the portion of the aircraft surface based on the predicted voltage levels in at least one of said graphical user interface sections;

showing a comparison of the predicted level of precipitation-static charge to material property values for the portion of the aircraft surface in at least one of said graphical user interface sections;

determining a size and location of an uncoated section defined by the portion of the aircraft surface based on the predicted level of precipitation-static charge on the surface based on one or more of said graphical user interface sections;

determining a need for repairs for the uncoated section based on one or more of said graphical user interface sections; and repairing the uncoated section based on the step of determining repairs for the uncoated section.

7. The method of claim 6, wherein the second input includes resistivity values for the uncoated portion of the surface and a coated portion of the surface.

8. The method of claim 6, further comprising displaying the plurality of curves corresponding to voltages at the surface at a plurality of conditions.

9. A computer-implemented system for determining and displaying occurrence of an arc over or arc through damage to an aircraft structure comprising a substrate section without a dielectric coating under specified conditions as well as a corresponding need to avoid exposure to such damage and repairs to the structure based on precipitation-static charge levels on the aircraft surface that is without the dielectric coating, including:

providing a display, input/output section, a computer processor, and a machine readable instructions storage medium comprising a plurality of non-transitory machine readable instructions, the plurality of non-transitory machine readable instructions comprising;

a first plurality of machine readable instructions that generates a graphical user interface input section shown on the display, the graphical user interface input section includes a first input for an electrical charge value associated with a charging environment comprising an atmospheric condition, a second input for a resistivity value associated with a dielectric coating, a third input for a velocity value, and a fourth input for a surface area value associated an uncoated substrate of an aircraft structure surrounded by the dielectric coating;

an input module comprising a second plurality of machine readable instructions that is configured to receive and store the first, second, third, and fourth inputs from the graphical user interface;

a calculation module comprising a third plurality of machine readable instructions that is configured to determine a predicted level of precipitation-static charge for the uncoated substrate of the aircraft structure through an integration of a plurality of charge potentials and a plurality of resistivity values along a portion of the surface defined by the surface area of the uncoated substrate;

a display module comprising a fourth plurality of machine readable instructions that is configured to generate and display on a monitor an output of the predicted level of precipitation-static charge with respect to the uncoated substrate area and physical separation to a conductive body comprising a ground to the user; and a determination module comprising a fifth plurality of machine readable instructions that outputs a determination graphical user interface comprising a plurality of graphical curves based on voltage versus a radius of coating damage associated with the uncoated substrate area, wherein the plurality of graphical curves are respectively based on multiple flight environments including dry snow, rain, and wet snow, the determination graphical user interface further comprises a damage indicator overlay defined by a line indicating the arc over or arc through damage occurrence at a combination of respective charging environments, velocities, and the portion of the aircraft surface that is overlaid over one or more of the curves, wherein the determination module is configured to indicate a location of the uncoated substrate and a repair status for the uncoated substrate.

* * * * *